US012636088B2

(12) United States Patent
Pluckter et al.

(10) Patent No.: US 12,636,088 B2
(45) Date of Patent: May 26, 2026

(54) IMAGE-BASED SEEDING FOR REGISTRATION AND ASSOCIATED SYSTEMS AND METHODS

(71) Applicant: INTUITIVE SURGICAL OPERATIONS, INC., Sunnyvale, CA (US)

(72) Inventors: Kevin X. Pluckter, Santa Clara, CA (US); Timothy D. Soper, San Jose, CA (US); Troy K. Adebar, San Jose, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 279 days.

(21) Appl. No.: 18/260,291

(22) PCT Filed: Dec. 27, 2021

(86) PCT No.: PCT/US2021/065195
§ 371 (c)(1),
(2) Date: Jul. 3, 2023

(87) PCT Pub. No.: WO2022/146911
PCT Pub. Date: Jul. 7, 2022

(65) Prior Publication Data
US 2024/0130799 A1 Apr. 25, 2024
US 2024/0225746 A9 Jul. 11, 2024

Related U.S. Application Data

(60) Provisional application No. 63/133,729, filed on Jan. 4, 2021.

(51) Int. Cl.
*A61B 34/20* (2016.01)
*A61B 34/10* (2016.01)

(52) U.S. Cl.
CPC .............. *A61B 34/20* (2016.02); *A61B 34/10* (2016.02); *A61B 2034/105* (2016.02);
(Continued)

(58) Field of Classification Search
CPC ... A61B 34/10; A61B 34/20; A61B 2034/105; A61B 2034/107; A61B 2034/2065; A61B 1/005; A61B 1/00055
See application file for complete search history.

(56) References Cited

U.S. PATENT DOCUMENTS

| | | |
|---|---|---|
| 5,389,187 A | 2/1995 | Marks et al. |
| 7,772,541 B2 | 8/2010 | Froggatt et al. |
| (Continued) | | |

FOREIGN PATENT DOCUMENTS

| | | | |
|---|---|---|---|
| WO | WO-2010133982 A2 | 11/2010 | |
| WO | WO-2017098505 A1 * | 6/2017 | ............. G06T 7/248 |

OTHER PUBLICATIONS

International Preliminary Report on Patentability for Application No. PCT/US2021/065195 mailed Jul. 13, 2023, 08 pages.
(Continued)

*Primary Examiner* — Joseph M Dietrich
(74) *Attorney, Agent, or Firm* — Haynes & Boone, LLP.

(57) ABSTRACT

Devices, systems, methods, and computer program products for performing medical procedures are disclosed herein. In some embodiments, a system for performing a medical procedure includes a medical instrument configured to be inserted within an anatomic region and including an image capture device. The system can receive a three-dimensional (3D) model of the anatomic region, the 3D model including a model landmark corresponding to an anatomic landmark in the anatomic region. The system can obtain, via the image capture device, a plurality of images of the anatomic landmark, at least some of the images representing different
(Continued)

views of the anatomic landmark. Based on the images, the system can determine a set of transformation parameters for aligning the anatomic landmark with the model landmark. The system can use the set of transformation parameters as a seed for registering the 3D model to the anatomic region.

20 Claims, 8 Drawing Sheets

(52) U.S. Cl.
    CPC . *A61B 2034/107* (2016.02); *A61B 2034/2059* (2016.02); *A61B 2034/2065* (2016.02)

(56)                     References Cited

U.S. PATENT DOCUMENTS

| | | | | |
|---|---|---|---|---|
| 7,781,724 | B2 | 8/2010 | Childers et al. | |
| 2006/0013523 | A1 | 1/2006 | Childlers et al. | |
| 2018/0235709 | A1 | 8/2018 | Donhowe et al. | |
| 2020/0000526 | A1* | 1/2020 | Zhao | A61B 34/35 |
| 2020/0297444 | A1* | 9/2020 | Camarillo | G16H 30/40 |
| 2022/0071715 | A1 | 3/2022 | Donhowe et al. | |
| 2022/0343504 | A1 | 10/2022 | Donhowe et al. | |

OTHER PUBLICATIONS

International Search Report and Written Opinion for Application No. PCT/US2021/065195, mailed Mar. 28, 2022, 14 pages.

Luo X., et al., "Advanced Endoscopic Navigation: Surgical Big Data, Methodology, and Applications," Annual Review of Biomedical Engineering, Jun. 2018, vol. 20 (1), pp. 221-251.

Mori K., et al., "Hybrid Bronchoscope Tracking Using a Magnetic Tracking Sensor and Image Registration," Medical image computing and computer-assisted intervention, Oct. 2005, vol. 8 (Pt 2), pp. 543-550.

Reynisson P., et al., "Navigated Bronchoscopy Technical Review," Journal of Bronchology & Interventional Pulmonology, Jul. 2014, vol. 21 (3), pp. 242-264.

Soper T.D., et al., "In Vivo Validation of a Hybrid Tracking System for Navigation of an Ultrathin Bronchoscope within Peripheral Airways," IEEE Transactions on Biomedical Engineering, 2010, vol. 57 (3), pp. 736-745.

Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.

* cited by examiner

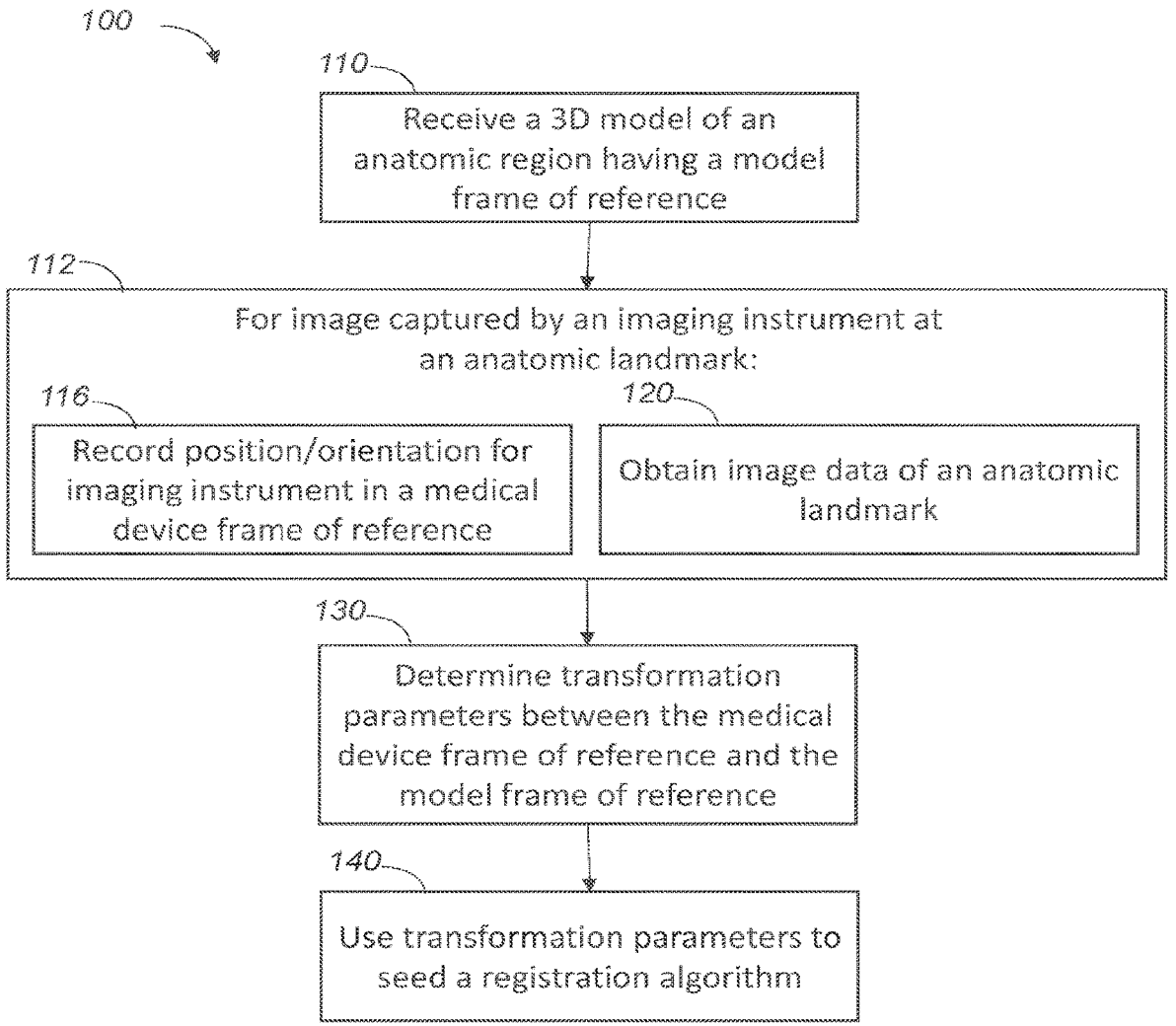

100

110 — Receive a 3D model of an anatomic region having a model frame of reference 112 — For image captured by an imaging instrument at an anatomic landmark:

116 — Record position/orientation for imaging instrument in a medical device frame of reference 120 — Obtain image data of an anatomic landmark 130 — Determine transformation parameters between the medical device frame of reference and the model frame of reference 140 — Use transformation parameters to seed a registration algorithm

*FIG. 1*

400a
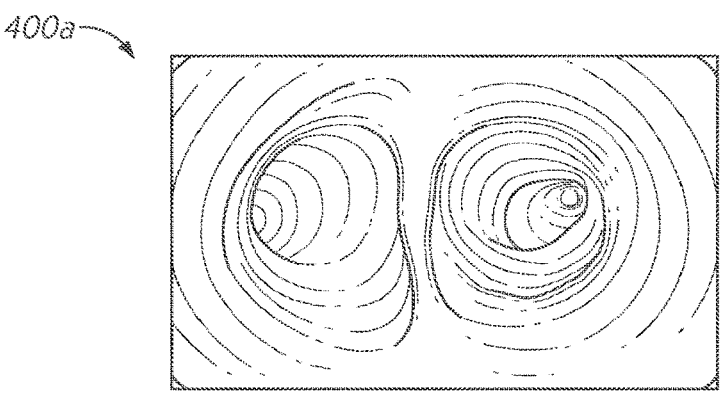
FIG. 4A
400b
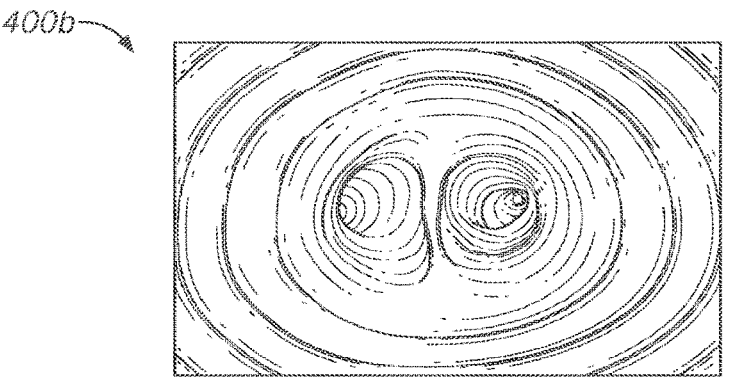
FIG. 4B
400c
400d
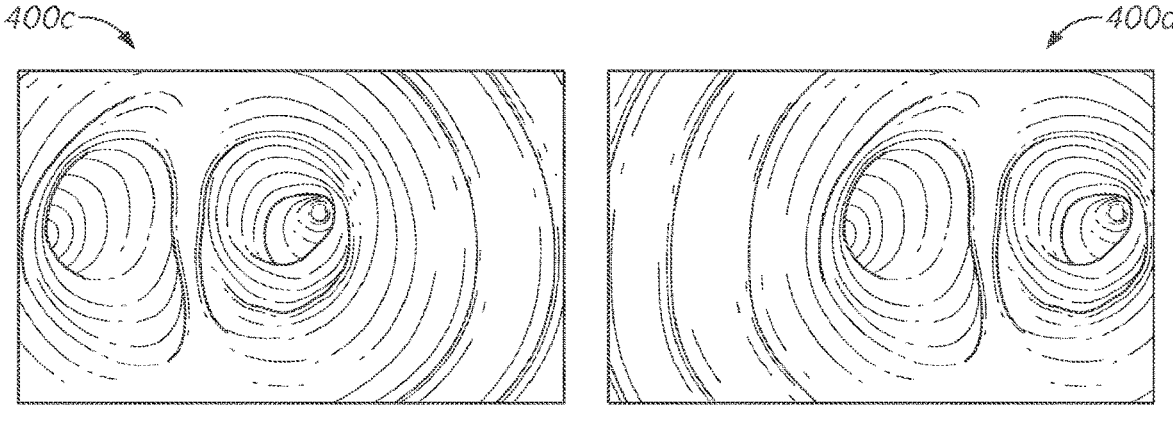
FIG. 4C                    FIG. 4D

1

IMAGE-BASED SEEDING FOR REGISTRATION AND ASSOCIATED SYSTEMS AND METHODS

CROSS-REFERENCE TO RELATED APPLICATIONS

This application is the U.S. National Stage patent application of International Patent Application No. PCT/US2021/065195 filed on Dec. 27, 2021 which claims the benefit of and priority to U.S. Provisional Application 63/133,729 filed Jan. 4, 2021, each of which is incorporated by reference herein in its entirety.

This application incorporates by reference in their entirety International Publication Number WO 2022/146918, titled "Systems for Dynamic Image-Based Localization and Associated Methods" and International Publication Number WO 2022/146919, titled "Systems for Image-Based Registration and Associated Methods."

TECHNICAL FIELD

The present disclosure is directed to systems, methods, and computer program products for seeding a registration algorithm for a medical procedure.

BACKGROUND

Minimally invasive medical techniques are intended to reduce the amount of tissue that is damaged during medical procedures, thereby reducing patient recovery time, discomfort, and harmful side effects. Such minimally invasive techniques may be performed through natural orifices in a patient anatomy or through one or more surgical incisions. Through these natural orifices or incisions, an operator may insert minimally invasive medical tools to reach a target tissue location. Minimally invasive medical tools include instruments such as therapeutic, diagnostic, biopsy, and surgical instruments. Medical tools may be inserted into anatomic passageways and navigated toward a region of interest within a patient anatomy. Navigation may be assisted using images of the anatomic passageways. Improved systems and methods are needed to accurately perform registrations between medical tools and images of the anatomic passageways.

SUMMARY

Disclosed herein are devices, systems, methods, and computer program products for performing medical procedures in a patient, such as generating a seed transformation for a registration algorithm. In some embodiments, a system for performing a medical procedure within an anatomic region of a patient includes a medical instrument configured to be inserted within the anatomic region, the medical instrument including an image capture device. The system can also include a processor operably coupled to the image capture device and a memory operably coupled to the processor. The memory can store instructions that, when executed by the processor, cause the system to perform operations including receiving a three-dimensional (3D) model of the anatomic region. The 3D model can include a model landmark corresponding to an anatomic landmark in the anatomic region. The operations can also include obtaining, via the image capture device, pose information for the image capture device and a plurality of images of the anatomic landmark. At least some of the images can represent different views of the anatomic landmark. The operations can further include determining, based on the pose information and the plurality of images, a set of transformation parameters for aligning a frame of reference for the image capture device with a frame of reference for the 3D model. The operations can also include registering the frame of reference for the 3D model to the frame of reference for the image capture device using a registration algorithm. The set of transformation parameters can be used as a seed for the registration algorithm.

In these and other embodiments, a non-transitory, computer-readable medium can store instructions that, when executed by one or more processors of a computing system, cause the computing system to perform operations including receiving a 3D model of an anatomic region, the 3D model including a model landmark corresponding to an anatomic landmark in the anatomic region. The operations can also include obtaining, via an image capture device within the anatomic region, pose information for the image capture device and a plurality of images of the anatomic landmark. At least some of the images can represent different views of the anatomic landmark. The operations can further include determining, based on the pose information and the plurality of images, a set of transformation parameters for aligning a frame of reference for the image capture device with a frame of reference for the 3D model. The operations can also include registering the frame of reference for the 3D model to the frame of reference for the image capture device using a registration algorithm. The set of transformation parameters can be used as a seed for the registration algorithm.

In these and still other embodiments, a method can include receiving a 3D model of an anatomic region, the 3D model including a model landmark corresponding to an anatomic landmark in the anatomic region. The method can also include obtaining, via an image capture device within the anatomic region, pose information for the image capture device and a plurality of images of the anatomic landmark. At least some of the images can represent different views of the anatomic landmark. The method can further include determining, based on the pose information and the plurality of images, a set of transformation parameters for aligning a frame of reference for the image capture device with a frame of reference for the 3D model. The method can also include registering the frame of reference for the 3D model to the frame of reference for the image capture device using a registration algorithm. The set of transformation parameters can be used as a seed for the registration algorithm.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure. The drawings should not be taken to limit the disclosure to the specific embodiments depicted but are for explanation and understanding only.

FIG. 1 is a flow diagram illustrating a method for determining a seed transformation for a registration algorithm in accordance with various embodiments of the present technology.

FIGS. 4A-4D illustrate a plurality of images obtained at the imaging locations of FIG. 3 in accordance with various embodiments of the present technology.

DETAILED DESCRIPTION

Figure 2:
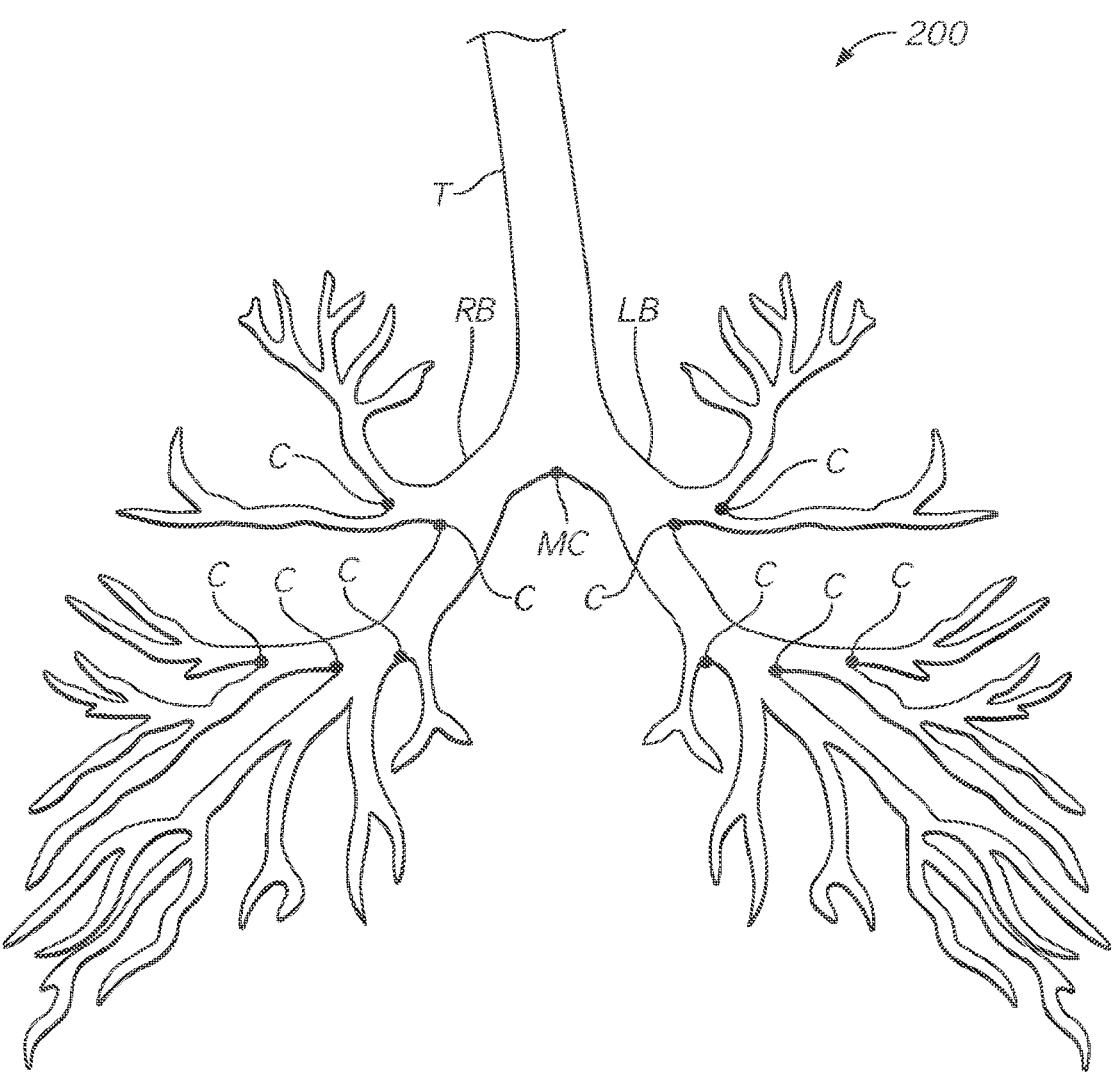
FIG. 2 illustrates examples of anatomic landmarks within the airways of a patient's lungs in accordance with various embodiments of the present technology.

The present disclosure is directed to devices, systems, methods, and computer program products for performing a medical procedure within an anatomic region of a patient. In some embodiments, an image-guided medical procedure uses a 3D model that is registered to the patient anatomy so that the position of a medical device within the patient can be tracked and mapped to a corresponding position within the model. The input data for the registration algorithm may include an initial estimate of the transformation parameters between the medical device frame of reference (or medical device coordinate frame) and the model frame of reference (or model coordinate frame) based on a correspondence between the patient anatomy and the model, also known as a "seed," "initial seed," or "seed transformation." An operator may generate the seed by manually aligning an endoscopic image of an anatomic landmark (e.g., the main carina of the airways) to a virtual image of a corresponding landmark in the model. However, this manual seeding process can be time-consuming and inefficient, and the operator may find it difficult to determine when the endoscopic and virtual images are sufficiently aligned for seeding purposes. Additionally, the registration may be inaccurate or otherwise impaired if the manually-generated seed is not sufficiently accurate.

Accordingly, the systems disclosed herein are expected to improve the seeding process by using image data to auto-matically or semi-automatically estimate the transformation parameters between the medical device frame of reference and the model frame of reference by determining the proper alignment between the anatomic landmark and the 3D model. In some embodiments, for example, the systems disclosed herein are configured to obtain image data of the anatomic landmark via an image capture device (e.g., an endoscopic camera) introduced into the patient anatomy. The system can use the image data to determine a set of transformation parameters (e.g., translation and/or rotation parameters) for aligning the anatomic landmark with a corresponding model landmark in the model, e.g., using two-dimensional (2D)-based and/or 3D-based image analy-sis techniques. Subsequently, the system can use the trans-formation parameters to determine the initial seed in a registration algorithm for registering the medical device frame of reference to the 3D model frame of reference. The present technology can improve the speed and accuracy of the seeding procedure by partially or fully automating processes that would otherwise have to be performed manu-ally by the operator.

A. EMBODIMENTS OF SEEDING PROCESSES

FIG. 1 is a flow diagram illustrating a method 100 for determining a seed transformation for a registration algo-rithm in accordance with various embodiments of the pres-ent technology. The method 100 is illustrated as a set of steps or processes 110-140. All or a subset of the steps of the method 100 can by implemented by any suitable computing system or device, such as a control system of a medical instrument system or device (e.g., including various com-ponents or devices of a robotic or teleoperated system), a workstation, a portable computing system (e.g., a laptop computer), and/or a combination thereof. In some embodi-ments, the computing system for implementing the method 100 includes one or more processors operably coupled to a memory storing instructions that, when executed, cause the computing system to perform operations in accordance with the steps 110-140. The method 100 is illustrated in the following description by cross-referencing various aspects of FIGS. 2, 3, and 4A-4D.

The method 100 begins at step 110 with receiving a 3D model of an anatomic region of a patient. The model may have a model frame of reference or coordinate frame. The model can represent an anatomic region in which a medical procedure is to be performed (e.g., the airways of the patient's lungs), and can represent the locations, shapes, and connectivity of the passageways and other structures within that region. In some embodiments, the model depicts one or more anatomic landmarks within the anatomic region. An anatomic landmark can be, or can include, any portion of the anatomic region that may be readily identified and/or dis-tinguished from other portions of the anatomic region, e.g., based on size, shape, color, and/or other suitable features. Examples of anatomic landmarks include, but are not lim-ited to: branching points or regions (e.g., carinas), passage-ways (e.g., airways), blood vessels (e.g., near or adjacent to a tissue surface), protrusions (e.g., ridges), apertures (e.g., airway openings or branches), or any other tissue structure with distinct features, or combinations thereof.

FIG. 2 illustrates examples of anatomic landmarks within the airways 200 of a patient's lungs in accordance with various embodiments of the present technology. As can be seen in FIG. 2, the airways 200 include a main carina MC at the point or region where the trachea T branches into the left main bronchus LB and right main bronchus RB. The airways 200 also include a plurality of carinas C correspond-ing to the locations of branching points or regions in the airways C. In some embodiments, the main carina MC serves as the sole anatomic landmark for the seeding procedures described herein. In other embodiments, however, any of the carinas C can be used as anatomic landmarks, in addition or alternatively to the main carina MC.

Referring again to FIG. 1, the 3D model of step 110 can be generated in a number of different ways. In some embodiments, for example, the 3D model is generated from preoperative and/or intraoperative image data of the anatomic region, such as computed tomography (CT) data, magnetic resonance imaging (MRI) data, fluoroscopy data, thermography data, ultrasound data, optical coherence tomography (OCT) data, thermal image data, impedance data, laser image data, nanotube X-ray image data, and/or other suitable data representing the patient anatomy. The image data can correspond to two-dimensional, 3D, or four-dimensional (e.g., time-based or velocity-based information) images. In some embodiments, for example, the image data includes two-dimensional images from multiple perspectives that can be combined into pseudo-3D images.

The 3D model can be generated by segmenting graphical elements in the image data that represent anatomic features. During the segmentation process, pixels or voxels generated from the image data may be partitioned into segments or elements and/or be tagged to indicate that they share certain characteristics or computed properties such as color, density, intensity, and texture. The segments or elements associated with anatomical features of the patient are then converted into a segmented anatomic model, which is generated in a model or image reference frame. To represent the model, the segmentation process may delineate sets of voxels representing the anatomic region and then apply a function, such as a marching cube function, to generate a 3D surface that encloses the voxels. The model may be made by generating a mesh, volume, or voxel map. Additionally or alternatively, the model may include a centerline model that includes a set of interconnected line segments or points extending through the centers of the modeled passageways. Where the model includes a centerline model including a set of interconnected line segments, those line segments may be converted to a cloud or set of points. By converting the line segments, a desired quantity of points corresponding to the interconnected line segments can be selected manually or automatically.

At step 112, the method 100 continues with capturing image information at an anatomic landmark including, including at step 116 recording position and/or orientation information of an image capture device and at step 120 obtaining image data of the anatomic landmark. The step 112 may be repeated for each of a plurality of captured images.

The step 116 includes recording position and/or orientation information of the image capture device. The pose (i.e., position and orientation) of the image capture device may be obtained when each image is taken. The pose data can be generated by one or more sensors associated with the image capture device, such as shape sensors, pose sensors, positional sensors, location sensors (e.g., electromagnetic (EM) sensors), etc. In such embodiments, the sensors can be coupled to the image capture device, or can be carried by a medical instrument or elongate device associated with the image capture device. The pose data can also be determined based on other information, such as insertion depth data, images from an external imaging device, control inputs from the operator, etc. The pose data can be used in combination with the image data in the subsequent image analysis and/or depth reconstruction processes discussed below. In some embodiments, for example, the image capture device is carried by a medical instrument inserted within the anatomic region. For example, as discussed in greater detail below with reference to FIGS. 5-11, the image capture device can be included in and/or mounted on a portion of the medical instrument, e.g., at or near the distal end portion of the medical instrument. As such, the pose of the image capture device can be identical or generally similar to the pose of the corresponding portion of the medical instrument. Additionally, as described further below with respect to FIGS. 5-11, the medical instrument can be deployed into the anatomic region via an elongate device (e.g., a steerable catheter), such that the pose of at least a portion of the medical instrument is identical or generally similar to a pose of the corresponding portion of the elongate device. Accordingly, any description herein regarding a position, orientation, pose, location, insertion depth, etc. of the image capture device can also refer to a position, orientation, pose, location, insertion depth, etc. of a corresponding portion of the medical instrument and/or elongate device, and vice-versa. Similarly, any description herein regarding movement of the image capture device (e.g., translating, rotating) can also refer to movement of a corresponding portion of the medical instrument and/or elongate device, and vice-versa.

The step 120 includes obtaining image data of at least one anatomic landmark in the anatomic region (e.g., the main carina of the airways) using the image capture device. The image data can be obtained by the image capture device (e.g., an endoscopic camera) configured to obtain images (e.g., still images, video image frames) from within the patient.

In some embodiments, step 120 includes capturing images of the anatomic landmark once the image capture device has been introduced into the anatomic region and moved sufficiently close to the anatomic landmark of interest. The process of determining whether the image capture device is sufficiently close to the anatomic landmark can be performed manually, automatically, or semi-automatically. For example, the operator can manually initiate image capture when the operator determines that the image capture device is sufficiently close to the anatomic landmark, e.g., based on image data from the image capture device, insertion depth data, positional data, image data of the image capture device and/or the medical instrument from an external imaging device, etc. In some embodiments, the operator views images generated by the image capture device to determine whether the image capture device is at a desired anatomic location (e.g., within the lungs or trachea) and/or whether the anatomic landmark (e.g., main carina) is within the field of view of the image capture device. Once the image capture device is positioned at an appropriate location for imaging the anatomic landmark, the operator can initiate imaging by providing a user input, such as pushing a button, typing or speaking a command, etc.

As another example, step 120 of the method 100 can include automatically detecting whether the image capture device is sufficiently close to the anatomic landmark for imaging (e.g., within 10 cm, 5 cm, 4 cm, 3 cm, 2 cm, 1.5 cm, 1 cm, or 0.5 cm of the anatomic landmark). In such embodiments, a computing system (or any other suitable system or device) can receive and analyze images generated by the image capture device to detect whether the image capture device is at a desired anatomic location and/or whether the anatomic landmark is within the field of view. The image analysis can be performed using any suitable technique, including machine learning algorithms (e.g., convolutional neural networks (CNNs)), circle detectors (e.g., the Hough transform), and/or other computer vision techniques. For instance, the analysis can include detecting anatomic landmarks in the image data (e.g., trachea, main carina, other carinas) based on features such as size, shape, number of visible branches (e.g., one visible branch when in the trachea versus two visible branches when near the main carina), changes in color, changes in texture, changes in intensity and so on. Proximity can additionally or alternatively be determined based on other types of data, such as insertion depth data, positional data, image data from an external imaging device, etc. For example, the image capture device can be considered to be sufficiently close to the anatomic landmark once the insertion depth of the image capture device and/or the medical instrument carrying the image capture device exceeds a predetermined threshold value. Once the image capture device is in proximity to the anatomic landmark, the system can automatically initiate imaging. Alternatively, the system can prompt the operator to initiate imaging, e.g., via textual, graphical, audio, and/or other types of output.

Optionally, in embodiments where the image capture device and medical instrument are introduced into the anatomic region via a separate introducer component (e.g., an elongate tube such as an endotracheal (ET) tube, etc.), step 120 of the method 100 can include automatically detecting whether the image capture device has been advanced past the distal end portion of the introducer component. For example, the detection process can use computer vision techniques (e.g., machine learning algorithms, circle detectors) to identify when the image capture device has exited the distal end of an ET tube, e.g., based on shape, changes in the size of visible branches (e.g., smaller when in the ET tube, larger when in the trachea), changes in color, changes in texture, etc. Optionally, the ET tube can include visual indicators, such as markings, patterning, color, etc. at or near its distal end, and the visual indicators can be used to determine the location of the image capture device relative to the end of the ET tube. Additional examples of visual indicators for an ET tube are described in further detail in U.S. Patent Application Publication No. 2018/0235709 (filed on Aug. 11, 2016) (disclosing systems and methods of registration for image-guided surgery), which is incorporated by reference herein in its entirety. Once the image capture device is deployed sufficiently far out of the introducer component, the system can automatically initiate imaging, or prompt the operator to do so.

In other embodiments, step 120 can involve initiating imaging at the start of the medical procedure (e.g., once the image capture device is powered on, once the operator begins driving the medical instrument, etc.), rather than waiting until the image capture device is close to the anatomic landmark. In such embodiments, the method 100 can include discarding image data that is irrelevant, erroneous, or otherwise not suitable for determining the initial seed (e.g., images taken before the image capture device enters the anatomic region and/or while the image capture device is still in the ET tube) in subsequent image analysis and/or depth reconstruction steps. For example, images that cannot be matched to any portion of the 3D model can be discarded, since such images are likely to have been taken while the image capture device was outside of the anatomic region. As another example, the discarded images can include images that produce 3D data that is clearly inconsistent with the 3D model (e.g., the centerline of the 3D data differs significantly from the centerline of the 3D model). Similarly, 3D data generated from images that do not contain landmarks essential to seeding the algorithm may likewise be discarded. In yet another example, step 120 can include tracking the location of the image capture device during imaging, and using the location data to discard images that were likely taken outside the anatomic region.

During the imaging process, the image capture device can obtain a plurality of images of the anatomic landmark, such as at least two, three, four, five, or more images. In some embodiments, some or all of the images are taken with the image capture device in different poses (e.g., different positions and/or orientations) relative to the anatomic landmark, such that the resulting images represent different views of the anatomic landmark. For example, images can be taken from at least two, three, four, five, or more different poses relative to the anatomic landmark. In other embodiments, however, the image capture device may take only a single image of the anatomic landmark from a single pose.

The number of images, as well as the amount of spatial offset and/or motion between the images, can be configured to allow the structure of the anatomic landmark to be reconstructed from the images, e.g., using 2D- and/or 3D-based reconstruction techniques as discussed in greater detail below. For example, the translational offset between images can be greater than or equal to, for example, 1 mm, 2 mm, 3 mm, 4 mm, 5 mm, 6 mm, 7 mm, 8 mm, 9 mm, 10 mm, 15 mm, 20 mm, 25 mm, 30 mm, 35 mm, 40 mm, 45 mm, or 50 mm. As another example, the rotational offset between images can be greater than or equal to, for example, 1 degree, 5 degrees, 10 degrees, 15 degrees, 20 degrees, 30 degrees, 40 degrees, 45 degrees, 50 degrees, or 60 degrees. The number of images and/or amount of offset between images may also vary based on the size of the local anatomy. For example, the image capture device can take more images with more spatial offset if the anatomic landmark is located within a relatively large anatomic passageway. Conversely, the image capture device can take fewer images with less spatial offset if the anatomic landmark is located within a smaller passageway. In some embodiments, when imaging an anatomic landmark in a narrow passageway with limited room for maneuvering, the image capture device may simply be moved in and out of the passageway during imaging. Conversely, when imaging an anatomic landmark in a wider passageway, the image capture device can also be turned in different directions relative to the landmark.

Figure 3:
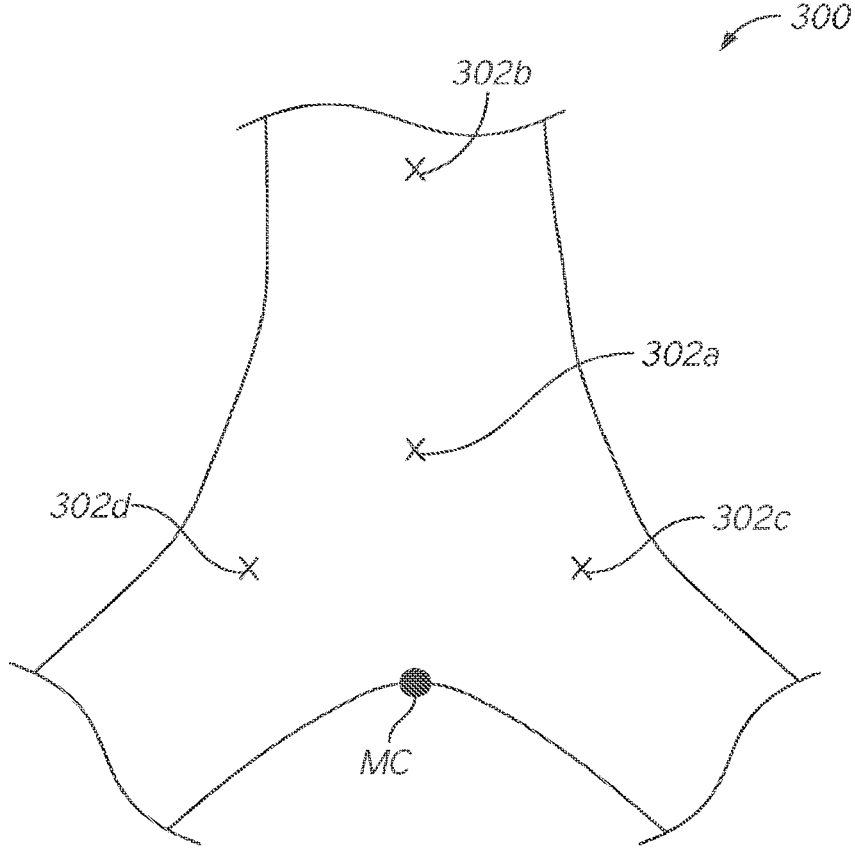
FIG. 3 illustrates a portion of a patient's airways including a plurality of imaging locations in accordance with various embodiments of the present technology.

FIG. 3 illustrates a portion 300 of a patient's airways and FIGS. 4A-4D illustrate a plurality of images 400a-400d of the portion 300 in accordance with various embodiments of the present technology. Referring first to FIG. 3, the airways include an anatomic landmark (e.g., main carina MC). An image capture device (not shown) can obtain a plurality of images of the main carina MC from a corresponding plurality of locations 302 (four are identified in FIG. 3 as 302a-d) relative to the main carina MC. For example, the image capture device can obtain image 400a (FIG. 4A) from location 302a at a first distance from the main carina MC, and image 400b (FIG. 4B) from location 302b at a second, greater distance from the main carina MC. As another example, the image capture device can obtain image 400c (FIG. 4C) from location 302c near a first (e.g., left) side of the main carina MC, and image 400d (FIG. 4D) from location 302d near a second (e.g., right) side of the main carina MC. In additional embodiments, the number, position, and/or orientation of the locations 302 may vary.

Referring again to FIG. 1, the image data of step 120 can be obtained in various ways, such as manually by the operator, automatically by a computing system (or other suitable system or device), or a combination thereof. In some embodiments, for example, the operator manually navigates the image capture device to different locations and obtains one or more images at each location. The system can provide instructions to guide the operator in navigating and obtaining suitable images. For example, the system can instruct the operator to move the image capture device to different positions and/or orientations relative to the anatomic landmark (e.g., "drive X distance forward," "drive in Y direction," "rotate Z degrees," etc.). As another example, the system can simply instruct the operator to collect a certain number of images of the anatomic landmark, without specifying specific positions and/or orientations of the image capture device. The instructions may be output as text, graphics (e.g., arrows or other visual indicators), audio, or any other suitable format.

Optionally, the system can track the location of the image capture device and update the instructions based on how the operator moves the image capture device. In some embodiments, the system detects whether the operator has obtained sufficient images at a specified location, and, if so, instructs the operator to drive the image capture device to the next location. If the system detects that there are gaps in the image data, the system can instruct the operator to obtain additional images, and, optionally, direct to the operator to specific locations where the additional images should be taken.

In some embodiments, the system automatically moves the image capture device to different locations relative to the anatomic landmark. For example, the system can determine a sequence of imaging locations (e.g., based on the size and/or shape of the local anatomy) or can use a predefined sequence (e.g., a predefined sequence of translations and/or rotation). Once the image capture device is at a specified location, the system can either automatically take one or more images from that location, or can prompt the operator to do so. Subsequently, the system can automatically move the image capture device to the next location. This process can be repeated until images have been taken from each location in the sequence.

Additionally, step 120 can include using the pose data to monitor the imaging process and, optionally, outputting appropriate instructions to the operator based on the pose data. For example, the pose data can be used to determine whether sufficient images have been obtained for a particular landmark and, if so, prompt the operator move the image capture device to a different pose. Here, sufficient images may be determined by the number of images, field of view, image overlap, or other factors to indicate sufficient viewing of a particular part of the airway anatomy. As another example, the pose data can be analyzed to detect whether images have not been taken from certain poses and instruct the operator to capture images from those poses. The pose data can also be used as feedback when automatically moving the image capture device to different poses, as discussed above.

Optionally, step 120 can involve implementing imaging techniques configured to ensure that the images contain sufficient features for the image analysis and/or depth reconstruction processes described in detail below. In some embodiments, for example, the anatomic landmark can be illuminated with different wavelengths of light (e.g., infrared, near-infrared, visible, etc.) to add and/or enhance features in the resulting images. For example, certain tissue structures such as blood vessels may be more apparent under certain wavelengths of light. Alternatively or in combination, structured light techniques can be used to add and/or enhance features of the anatomy by projecting a known geometric pattern onto the imaging target (e.g., grid, stripes, bars, etc.).

Step 120 of the method 100 can also include providing feedback to assist the operator in collecting higher quality images (e.g., via a graphical user interface and/or other output). For example, such feedback can alert the operator of issues that may compromise image quality such as blurring, fogging, and/or obstruction of the image capture device (e.g., by blood and/or other bodily fluids). The feedback can also instruct the operator to perform one or more recommended actions to resolve the issue, such as defogging the image capture device, clearing obstructions from the image capture device, moving the image capture device to a different location, etc. Optionally, the system can also perform corrective actions automatically, e.g., activating defogging and/or cleaning mechanisms to clear the image capture device. As another example, in embodiments where the imaging is performed within narrow and/or tortuous passageways (e.g., airways), the feedback can periodically remind the operator to keep the image capture device away from the walls of the passageways to avoid obstructing the field of view. In some embodiments, the system is configured to detect whether the image capture device is too close to the walls of the passageways (e.g., using image analysis, sensors to detect friction and/or resistance to movement, etc.) and prompt the operator to take corrective action, if appropriate. Additionally, the system can automatically detect and tag poor quality images (e.g., blurry images, images with obstructions) so they can be excluded in subsequent process steps.

At step 130, the method 100 comprises determining one or more transformation parameters between the medical device frame of reference and the model frame of reference, based on the image data. The transformation parameters can represent a correspondence or mapping between the anatomic landmark and a corresponding model landmark in the 3D model. For example, the transformation parameters can include one or more translations, rotations, and/or other rigid or non-rigid transformations to align the anatomic landmark with the model landmark. The transformation parameters can be used to seed a registration between the patient anatomy and the 3D model, as discussed in greater detail below. In some examples, because the medical device frame of reference has a known correspondence (based, for example on a kinematic chain and/or sensor information) to a frame of reference for a robot-assisted manipulator assembly (e.g. manipulator assembly 502), the transformation parameters may also provide a transformation between the robot-assisted manipulator assembly and the 3D model.

The transformation parameters can be determined from the image data using a 2D-based approach, a 3D-based approach, or a combination thereof. For example, a 2D image analysis process can include determining a correspondence between one or more images of the anatomic landmark obtained in step 120 (also referred to herein as "real images") and one or more images of the model landmark generated from the 3D model (also referred to herein as "virtual views" or "virtual images"). Each virtual view can be a 2D image representing the viewpoint from a particular location within the 3D model. In some embodiments, the analysis uses a 2D image alignment algorithm (e.g., an inverse-compositional Lucas-Kanade algorithm) to determine the correspondence between the real images and virtual views. The inputs to the 2D image alignment algorithm can include, for example, one or more real images, the pose of the image capture device when the real images were taken, one or more virtual views, and/or the pose of the viewpoints used to generate the virtual views. The algorithm can analyze the real images and virtual views to detect and extract 2D image features, such as points, edges, corners, blobs, ridges, changes in intensity, changes in color, etc. The features can include sparse features, dense features, or a combination thereof. The features from the real images and virtual views can then be compared to identify similar and/or matching features (e.g., features that are present in both the real images and the virtual views). Subsequently, the identified features can be used to determine a set of alignment parameters (e.g., translations, rotations, warping, etc.) to map one or more real images to one or more virtual views. The alignment parameters can be used as the transformation parameters between the anatomic landmark and the model landmark, or can be used to calculate the transformation parameters (e.g., in combination with other inputs such as the location and/or pose of the image capture device). In one embodiment, the set of transformation parameters may be optimized by an iterative process in which virtual views are regenerated from the 3D model and transformation parameters at each iteration. In this approach, transformation parameters are iteratively improved until alignment between 2D real and virtual images is maximized.

Alternatively or in combination, the transformation parameters between the anatomic landmark and the 3D model can be determined using a 3D depth reconstruction process. For example, the image data of the anatomic landmark obtained in step 120 can be used to generate a 3D representation or reconstruction of the anatomic landmark, such as a surface or mesh model, a 3D point cloud, etc. The 3D reconstruction can be generated using any suitable technique for determining 3D depth information from one or more 2D images, such as structure from motion, shape from shading, and/or machine learning-based techniques (e.g., single shot depth estimation, end-to-end depth reconstruction, etc.). For example, a machine learning model (e.g., a CNN) can be trained to generate a 3D depth map of the anatomy from one or more 2D images. As another example, 3D depth data can be estimated from 2D images using sparse or dense depth reconstruction techniques. Additionally, the pose data of the image capture device can be used to determine scale information for the 3D reconstruction. Once the 3D reconstruction has been generated, the system can determine an alignment between the 3D reconstruction of the anatomic landmark and the model landmark in the 3D model. The alignment can be determined using a 3D alignment or registration algorithm, such as an iterative closest point (ICP) algorithm, an ICP with scaling algorithm, a surface- or mesh-based ICP algorithm, a coherent point drift algorithm, or a machine learning-based algorithm (e.g., PointNetLK). Optionally, the 3D reconstruction and 3D model can be analyzed and compared to identify similar and/or matching surface features (e.g., features that are present in both the 3D reconstruction and 3D model). The correspondence between these identified features can provide additional input (e.g., constraints) for the alignment algorithm. The output of the alignment algorithm can be the transformation parameters between the anatomic landmark and the model landmark.

Optionally, step 130 can further include providing feedback to the operator if it determines that the image data is insufficient for the image analysis and/or depth reconstruction processes described herein (e.g., portions of the anatomic landmark have not been adequately imaged, the real images cannot be adequately aligned with the virtual views, there are gaps in the 3D reconstruction, the 3D reconstruction cannot be adequately aligned with the 3D model, etc.). For example, the feedback can instruct the operator to obtain additional image data, and can use such additional image data in combination with, or as an alternative to, the previous image data to determine the transformation parameters. Accordingly, steps 120 and 130 can be repeated multiple times to iteratively refine the results of the image analysis and/or depth reconstruction.

At step 140, the method 100 includes using the transformation parameters to seed a registration algorithm. The registration algorithm can determine a correspondence between the medical device frame of reference and the model frame of reference, and the transformation parameters can provide an initial estimate of the correspondence to seed the algorithm. The registration process can be performed, for example, using a point-based ICP technique, as described in U.S. Provisional Pat. App. Nos. 62/205,440 and No. 62/205, 433, which are both incorporated by reference herein in their entireties. In some embodiments, for example, the operator drives the medical instrument within the anatomic region to obtain a plurality of coordinate points (e.g., a point cloud). The coordinate points can be generated by a positional and/or shape sensor carried by the instrument, as discussed in greater detail below. To seed the registration algorithm, the transformation parameters determined in step 130 can be applied to the coordinate points to provide an initial, coarse alignment with the 3D model. Subsequently, the registration algorithm can modify and/or refine the initial alignment, e.g., by rotating, translating, and/or otherwise manipulating the coordinate points by rigid and/or non-rigid transformations to align them with the data points of the model. Once the registration has been performed, the operator can use the registration for performing an image-guided medical procedure in the anatomic region (e.g., navigating a biopsy instrument to a target lesion).

Although the steps of the method 100 are discussed and illustrated in a particular order, a person of ordinary skill in the relevant art will recognize that the method 100 can be altered and still remain within these and other embodiments of the present technology. In other embodiments, for example, the method 100 can be performed in a different order, e.g., any of the steps of the method 100 can be performed before, during, and/or after any of the other steps of the method 100. For example, step 120 can be performed before and/or concurrently with step 110. Additionally, one or more steps of the method 100 illustrated in FIG. 1 can be omitted. Optionally, one or more steps of the method 100 can be repeated. For example, in embodiments where different portions of the anatomic region are individually registered to the model in separate processes, steps 120-140 can be repeated multiple times to determine a seed transformation for each registration.

B. EMBODIMENTS OF ROBOTIC OR TELEOPERATED MEDICAL SYSTEMS AND ASSOCIATED DEVICES, SYSTEMS, AND METHODS

Figure 5:
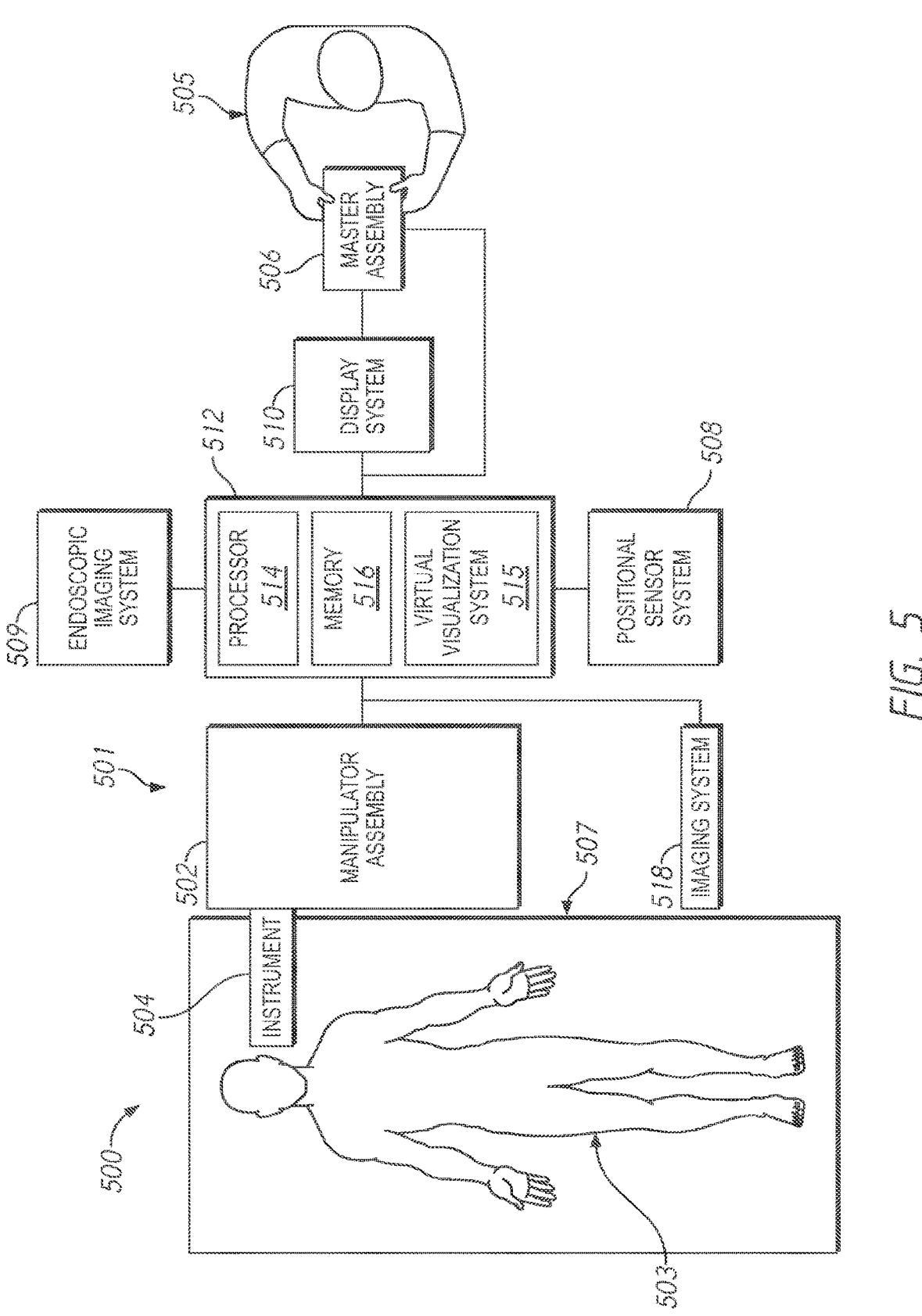
FIG. 5 is a schematic representation of a robotic or teleoperated medical system configured in accordance with various embodiments of the present technology.

FIG. 5 is a schematic representation of a robotic or teleoperated medical system 500 ("medical system 500") configured in accordance with various embodiments of the present technology. The medical system 500 can be used with any of the procedures or methods described above with respect to FIGS. 1-4D. For example, the medical system 500 can be used to capture images of an anatomic landmark to determine a seed transformation for a registration algorithm, as previously discussed. As shown, the medical system 500 includes a manipulator assembly 502, a medical instrument system 504, a master assembly 506, and a control system 512. The manipulator assembly 502 supports the medical instrument system 504 and drives the medical instrument system 504 at the direction of the master assembly 506 and/or the control system 512 to perform various medical procedures on a patient 503 positioned on a table 507 in a surgical environment 501. In this regard, the master assembly 506 generally includes one or more control devices that can be operated by an operator 505 (e.g., a physician) to control the manipulator assembly 502. Additionally, or alternatively, the control system 512 includes a computer processor 514 and at least one memory 516 for effecting control between the medical instrument system 504, the master assembly 506, and/or other components of the medical system 500. The control system 512 can also include programmed instructions (e.g., a non-transitory computer-readable medium storing the instructions) to implement any one or more of the methods described herein, including instructions for providing information to a display system 510 and/or processing data for registration of the medical instrument system 504 with an anatomical model of the patient 503 (as described in greater detail below). The manipulator assembly 502 can be a teleoperated, a non-teleoperated, or a hybrid teleoperated and non-teleoperated assembly. Thus, all or a portion of the master assembly 506 and/or all or a portion of the control system 512 can be positioned inside or outside of the surgical environment 501.

To aid the operator 505 in controlling the manipulator assembly 502 and/or the medical instrument system 504 during an image-guided medical procedure, the medical system 500 may further include a positional sensor system 508, an endoscopic imaging system 509, an imaging system 518, and/or a virtual visualization system 515. In some embodiments, the positional sensor system 508 includes a location sensor system (e.g., an electromagnetic (EM) sensor system) and/or a shape sensor system for capturing positional sensor data (e.g., position, orientation, speed, velocity, pose, shape, etc.) of the medical instrument system 504. In these and other embodiments, the endoscopic imaging system 509 includes one or more image capture devices (not shown) that record endoscopic image data that includes concurrent or real-time images (e.g., video, still images, etc.) of patient anatomy. Images captured by the endoscopic imaging system 509 may be, for example, two or three-dimensional images of patient anatomy captured by an image capture device positioned within the patient 503, and are referred to hereinafter as "real navigational images."

In some embodiments, the medical instrument system 504 may include components of the positional sensor system 508 and/or components of the endoscopic imaging system 509. For example, components of the positional sensor system 508 and/or components of the endoscopic imaging system 509 can be integrally or removably coupled to the medical instrument system 504. Additionally, or alternatively, the endoscopic imaging system 509 can include a separate endoscope (not shown) attached to a separate manipulator assembly (not shown) that can be used in conjunction with the medical instrument system 504 to image patient anatomy. The positional sensor system 508 and/or the endoscopic imaging system 509 may be implemented as hardware, firmware, software, or a combination thereof that interact with or are otherwise executed by one or more computer processors, such as the computer processor(s) 514 of the control system 512.

The imaging system 518 of the medical system 500 may be arranged in the surgical environment 501 near the patient 503 to obtain real-time and/or near real-time images of the patient 503 before, during, and/or after a medical procedure. In some embodiments, the imaging system 518 includes a mobile C-arm cone-beam CT imaging system for generating three-dimensional images. For example, the imaging system 518 can include a DynaCT imaging system from Siemens Corporation, or another suitable imaging system. In these and other embodiments, the imaging system 518 can include other imaging technologies, including MRI, fluoroscopy, thermography, ultrasound, OCT, thermal imaging, impedance imaging, laser imaging, nanotube X-ray imaging, and/or the like.

The virtual visualization system 515 of the control system 512 provides navigation and/or anatomy-interaction assistance to the operator 505 when controlling the medical instrument system 504 during an image-guided medical procedure. As described in greater detail below, virtual navigation using the virtual visualization system 515 can be based, at least in part, upon reference to an acquired pre-operative or intra-operative dataset (e.g., based, at least in part, upon reference to data generated by the positional sensor system 508, the endoscopic imaging system 509, and/or the imaging system 518) of anatomic passageways of the patient 503. In some implementations, for example, the virtual visualization system 515 processes preoperative and/or intraoperative image data of an anatomic region of the patient 503 captured by the imaging system 518 to generate an anatomic model (not shown) of the anatomic region. The virtual visualization system 515 then registers the anatomic model to positional sensor data generated by the positional sensor system 508 and/or to endoscopic image data generated by the endoscopic imaging system 509 to (i) map the tracked position, orientation, pose, shape, and/or movement of the medical instrument system 504 within the anatomic region to a correct position within the anatomic model, and/or (ii) determine a virtual navigational image of virtual patient anatomy of the anatomic region from a viewpoint of the medical instrument system 504 at a location within the anatomic model corresponding to a location of the medical instrument system 504 within the patient 503.

The display system 510 can display various images or representations of patient anatomy and/or of the medical instrument system 504 that are generated by the positional sensor system 508, by the endoscopic imaging system 509, by the imaging system 518, and/or by the virtual visualization system 515. In some embodiments, the display system 510 and/or the master assembly 506 may be oriented so the operator 505 can control the manipulator assembly 502, the medical instrument system 504, the master assembly 506, and/or the control system 512 with the perception of telepresence.

As discussed above, the manipulator assembly 502 drives the medical instrument system 504 at the direction of the master assembly 506 and/or the control system 512. In this regard, the manipulator assembly 502 can include select degrees of freedom of motion that may be motorized and/or teleoperated and select degrees of freedom of motion that may be non-motorized and/or non-teleoperated. For example, the manipulator assembly 502 can include a plurality of actuators or motors (not shown) that drive inputs on the medical instrument system 504 in response to commands received from the control system 512. The actuators can include drive systems (not shown) that, when coupled to the medical instrument system 504, can advance the medical instrument system 504 into a naturally or surgically created anatomic orifice. Other drive systems may move a distal portion (not shown) of the medical instrument system 504 in multiple degrees of freedom, which may include three degrees of linear motion (e.g., linear motion along the X, Y, Z Cartesian axes) and three degrees of rotational motion (e.g., rotation about the X, Y, Z Cartesian axes). Additionally, or alternatively, the actuators can be used to actuate an articulable end effector of the medical instrument system 504 (e.g., for grasping tissue in the jaws of a biopsy device and/or the like).

Figure 6:
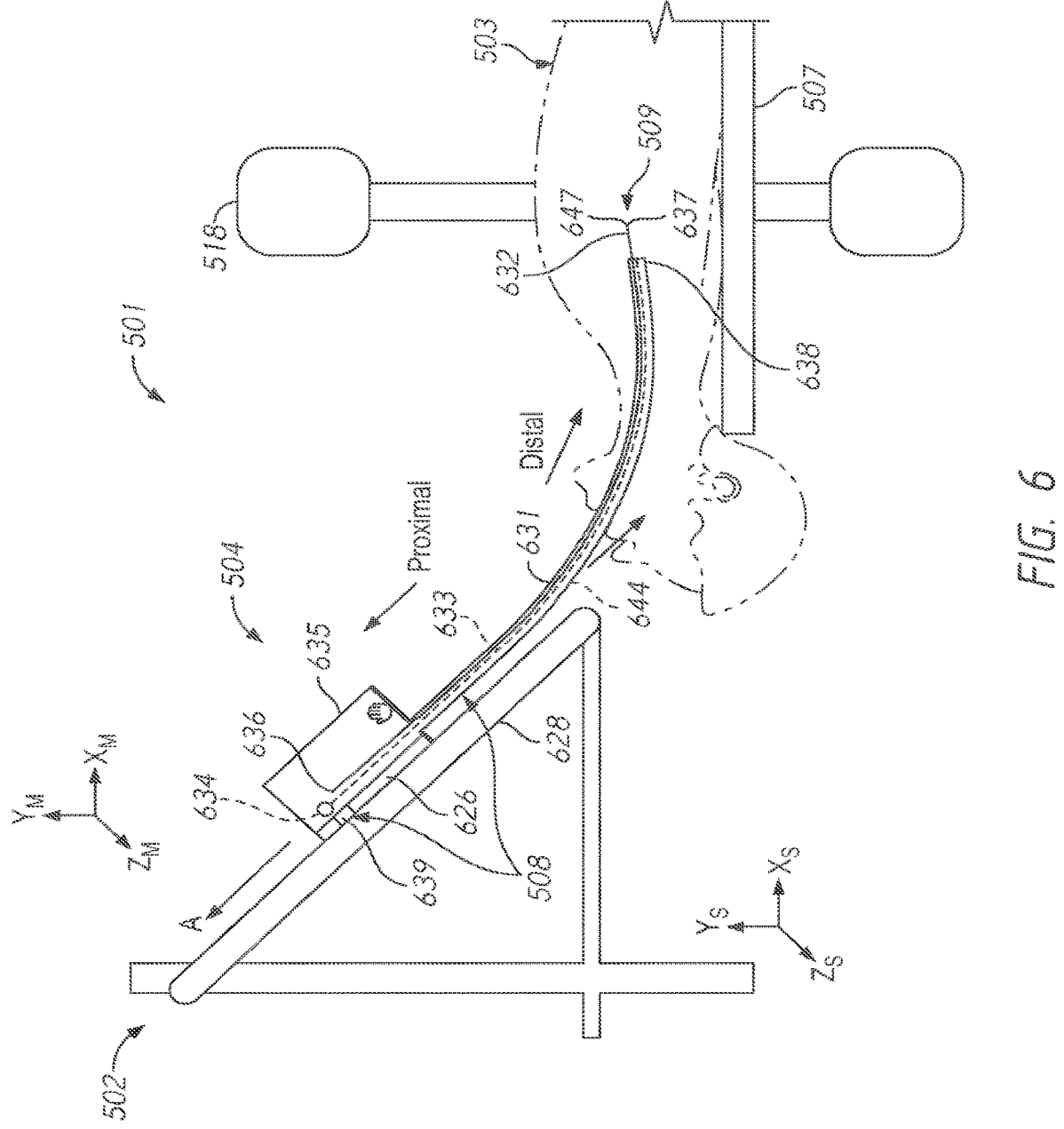
FIG. 6 is a schematic representation of a manipulator assembly, a medical instrument system, and an imaging system configured in accordance with various embodiments of the present technology.

FIG. 6 is a schematic representation of the manipulator assembly 502, the medical instrument system 504, and the imaging system 518 of FIG. 5 within the surgical environment 501 and configured in accordance with various embodiments of the present technology. As shown in FIG. 6, the surgical environment 501 has a surgical frame of reference $(X_S, Y_S, Z_S)$ in which the patient 503 is positioned on the table 507, and the medical instrument system 504 has a medical instrument frame of reference $(X_M, Y_M, Z_M)$ within the surgical environment 501. During the medical procedure, the patient 503 may be stationary within the surgical environment 501 in the sense that gross patient movement can be limited by sedation, restraint, and/or other means. In these and other embodiments, cyclic anatomic motion of the patient 503, including respiration and cardiac motion, may continue unless the patient 503 is asked to hold his or her breath to temporarily suspend respiratory motion.

The manipulator assembly 502 includes an instrument carriage 626 mounted to an insertion stage 628. In the illustrated embodiment, the insertion stage 628 is linear, while in other embodiments, the insertion stage 628 is curved or has a combination of curved and linear sections. In some embodiments, the insertion stage 628 is fixed within the surgical environment 501. Alternatively, the insertion stage 628 can be movable within the surgical environment 501 but have a known location (e.g., via a tracking sensor (not shown) or other tracking device) within the surgical environment 501. In these alternatives, the medical instrument frame of reference $(X_M, Y_M, Z_M)$ is fixed or otherwise known relative to the surgical frame of reference $(X_S, Y_S, Z_S)$.

The medical instrument system 504 of FIG. 6 includes an elongate device 631, a medical instrument 632, an instrument body 635, at least a portion of the positional sensor system 508, and at least a portion of the endoscopic imaging system 509. In some embodiments, the elongate device 631 is a flexible catheter or other biomedical device that defines a channel or lumen 644. The channel 644 can be sized and shaped to receive the medical instrument 632 (e.g., via a proximal end 636 of the elongate device 631 and/or an instrument port (not shown)) and facilitate delivery of the medical instrument 632 to a distal portion 638 of the elongate device 631. The elongate device 631 is coupled to the instrument body 635, which in turn is coupled and fixed relative to the instrument carriage 626 of the manipulator assembly 502.

In operation, the manipulator assembly 502 can control insertion motion (e.g., proximal and/or distal motion along an axis A) of the elongate device 631 into the patient 503 via a natural or surgically created anatomic orifice of the patient 503 to facilitate navigation of the elongate device 631 through anatomic passageways of an anatomic region of the patient 503 and/or to facilitate delivery of a distal portion 638 of the elongate device 631 to or near a target location within the patient 503. For example, the instrument carriage 626 and/or the insertion stage 628 may include actuators (not shown), such as servomotors, that facilitate control over motion of the instrument carriage 626 along the insertion stage 628. Additionally, or alternatively, the manipulator assembly 502 in some embodiments can control motion of the distal portion 638 of the elongate device 631 in multiple directions, including yaw, pitch, and roll rotational directions (e.g., to navigate patient anatomy). To this end, the elongate device 631 may house or include cables, linkages, and/or other steering controls (not shown) that the manipulator assembly 502 can use to controllably bend the distal portion 638 of the elongate device 631. For example, the elongate device 631 can house at least four cables that can be used by the manipulator assembly 502 to provide (i) independent "up-down" steering to control a pitch of the distal portion 638 of the elongate device 631 and (ii) independent "left-right" steering of the elongate device 631 to control a yaw of the distal portion 638 of the elongate device 631.

The medical instrument 632 of the medical instrument system 504 can be used for medical procedures, such as for survey of anatomic passageways, surgery, biopsy, ablation, illumination, irrigation, and/or suction. Thus, the medical instrument 632 can include image capture probes, biopsy instruments, laser ablation fibers, and/or other surgical, diagnostic, and/or therapeutic tools. For example, the medical instrument 632 can include an endoscope or other biomedical device having one or more image capture devices 647 positioned at a distal portion 637 of and/or at other locations along the medical instrument 632. In these embodiments, an image capture device 647 can capture one or more real navigational images or video (e.g., a sequence of one or more real navigational image frames) of anatomic passageways and/or other real patient anatomy while the medical instrument 632 is within an anatomic region of the patient 503.

As discussed above, the medical instrument 632 can be deployed into and/or be delivered to a target location within the patient 503 via the channel 644 defined by the elongate device 631. In embodiments in which the medical instrument 632 includes an endoscope or other biomedical device having an image capture device 647 at its distal portion 637, the image capture device 647 can be advanced to the distal portion 638 of the elongate device 631 before, during, and/or after the manipulator assembly 502 navigates the distal portion 638 of the elongate device 631 to a target location within the patient 503. In these embodiments, the medical instrument 632 can be used as a survey instrument to capture real navigational images of anatomic passageways and/or other real patient anatomy, and/or to aid an operator (not shown) to navigate the distal portion 638 of the elongate device 631 through anatomic passageways to the target location.

As another example, after the manipulator assembly 502 positions the distal portion 638 of the elongate device 631 proximate a target location within the patient 503, the medical instrument 632 can be advanced beyond the distal portion 638 of the elongate device 631 to perform a medical procedure at the target location. Continuing with this example, after all or a portion of the medical procedure at the target location is complete, the medical instrument 632 can be retracted back into the elongate device 631 and, additionally or alternatively, be removed from the proximal end 636 of the elongate device 631 or from another instrument port (not shown) along the elongate device 631.

As shown in FIG. 6, the positional sensor system 508 of the medical instrument system 504 includes a shape sensor 633 and a position measuring device 639. In these and other embodiments, the positional sensor system 508 can include other position sensors (e.g., accelerometers, rotary encoders, etc.) in addition to or in lieu of the shape sensor 633 and/or the position measuring device 639.

The shape sensor 633 of the positional sensor system 508 includes an optical fiber extending within and aligned with the elongate device 631. In one embodiment, the optical fiber of the shape sensor 633 has a diameter of approximately 200 μm. In other embodiments, the diameter of the optical fiber may be larger or smaller. The optical fiber of the shape sensor 633 forms a fiber optic bend sensor that is used to determine a shape, orientation, and/or pose of the elongate device 631. In some embodiments, optical fibers having Fiber Bragg Gratings (FBGs) can be used to provide strain measurements in structures in one or more dimensions. Various systems and methods for monitoring the shape and relative position of an optical fiber in three dimensions are described in further detail in U.S. Patent Application Publication No. 2006/0013523 (filed Jul. 13, 2005) (disclosing fiber optic position and shape sensing device and method relating thereto); U.S. Pat. No. 7,781,724 (filed on Sep. 26, 2006) (disclosing fiber-optic position and shape sensing device and method relating thereto); U.S. Pat. No. 7,772,541 (filed on Mar. 12, 2008) (disclosing fiber-optic position and/or shape sensing based on Rayleigh scatter); and U.S. Pat. No. 5,389,187 (filed on Jun. 17, 1998) (disclosing optical fiber bend sensors), which are all incorporated by reference herein in their entireties. In these and other embodiments, sensors of the present technology may employ other suitable strain sensing techniques, such as Rayleigh scattering, Raman scattering, Brillouin scattering, and Fluorescence scattering. In these and still other embodiments, the shape of the elongate device 631 may be determined using other techniques. For example, a history of the pose of the distal portion 638 of the elongate device 631 can be used to reconstruct the shape of elongate device 631 over an interval of time.

In some embodiments, the shape sensor 633 is fixed at a proximal point 634 on the instrument body 635 of the medical instrument system 504. In operation, for example, the shape sensor 633 measures a shape in the medical instrument reference frame ($X_M$, $Y_M$, $Z_M$) from the proximal point 634 to another point along the optical fiber, such as the distal portion 638 of the elongate device 631. The proximal point 634 of the shape sensor 633 may be movable along with instrument body 635 but the location of proximal point 634 may be known (e.g., via a tracking sensor (not shown) or other tracking device).

The position measuring device 639 of the positional sensor system 508 provides information about the position of the instrument body 635 as it moves along the insertion axis A on the insertion stage 628 of the manipulator assembly 502. In some embodiments, the position measuring device 639 includes resolvers, encoders, potentiometers, and/or other sensors that determine the rotation and/or orientation of actuators (not shown) controlling the motion of the instrument carriage 626 of the manipulator assembly 502 and, consequently, the motion of the instrument body 635 of the medical instrument system 504.

Figures 7, 8, 9, 10:
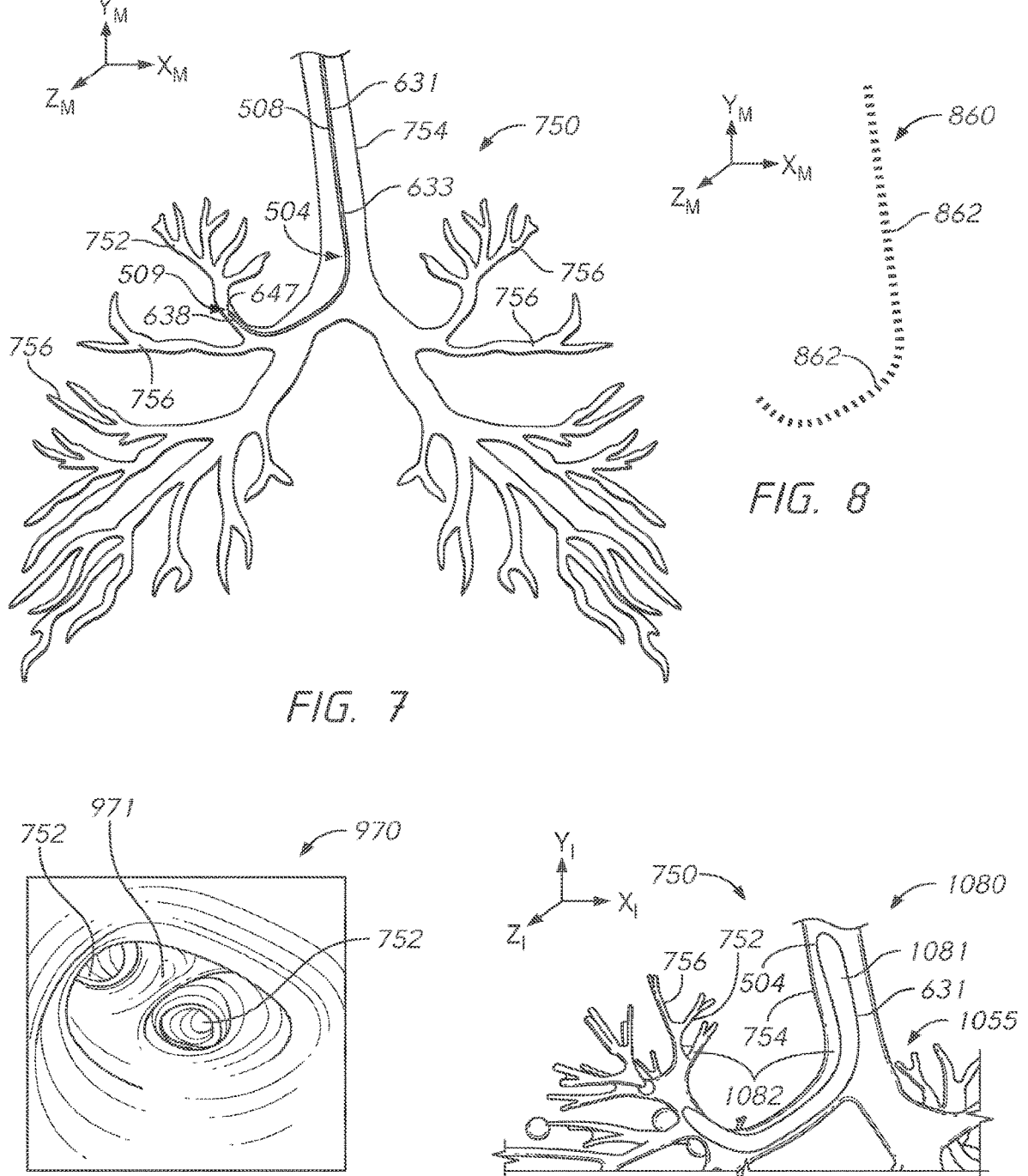
FIG. 7 is a schematic representation of a portion of the medical instrument system of FIG. 6 extended within an anatomic region of a patient in accordance with various embodiments of the present technology.
FIG. 8 illustrates a plurality of coordinate points forming a point cloud representing a shape of the portion of the medical instrument system of FIG. 7 configured in accordance with various embodiments of the present technology.
FIG. 9 illustrates a real navigational image of real patient anatomy from a viewpoint of the portion of the medical instrument system of FIG. 7 extended within the anatomic region of FIG. 7 in accordance with various embodiments of the present technology.
FIG. 10 illustrates an intraoperative image of a portion of the anatomic region of FIG. 7 while the portion of the medical instrument system of FIG. 7 is extended within the anatomic region in accordance with various embodiments of the present technology.

FIG. 7 is a schematic representation of a portion of the medical instrument system 504 of FIG. 6 extended within an anatomic region 750 (e.g., human lungs) of the patient 503 in accordance with various embodiments of the present technology. In particular, FIG. 7 illustrates the elongate device 631 of the medical instrument system 504 extending within branched anatomic passageways 752 of the anatomic region 750. The anatomic passageways 752 include a trachea 754 and a plurality of bronchial tubes 756.

As shown in FIG. 7, the elongate device 631 has a position, orientation, pose, and shape within the anatomic region 750, all or a portion of which (in addition to or in lieu of movement, such as speed or velocity) can be captured as positional sensor data by the positional sensor system 508 of FIGS. 5 and 6 (e.g., by the shape sensor 633 and/or the position measuring device 639 (FIG. 6)) to survey the anatomic passageways 752 of the anatomic region 750. In particular, the positional sensor system 508 can survey the anatomic passageways 752 by gathering positional sensor data of the medical instrument system 504 within the anatomic region 750 in the medical instrument frame of reference ($X_M$, $Y_M$, $Z_M$). The positional sensor data may at least in part be recorded as a set of two-dimensional or three-dimensional coordinate points. In the example of the anatomic region 750 being human lungs, the coordinate points may represent the locations of the distal portion 638 of the elongate device 631 and/or of other portions of the elongate device 631 while the elongate device 631 is advanced through the trachea 754 and the bronchial tubes 756. In these and other embodiments, the collection of coordinate points may represent the shape(s) of the elongate device 631 while the elongate device 631 is advanced through the anatomic region 750. In these and still other embodiments, the coordinate points may represent positional data of other portions (e.g., the medical instrument 632 (FIG. 6)) of the medical instrument system 504.

The coordinate points may together form a point cloud. For example, FIG. 8 illustrates a plurality of coordinate points 862 forming a point cloud 860 representing a shape of the elongate device 631 of FIG. 7 while the elongate device 631 is within the anatomic region 750 (FIG. 7) in accordance with various embodiments of the present technology. In particular, the point cloud 860 of FIG. 8 is generated from the union of all or a subset of the coordinate points 862 recorded by the positional sensor system 508 (FIG. 6) while the elongate device 631 is in the stationary position illustrated in FIG. 7.

In some embodiments, a point cloud (e.g., the point cloud 860) can include the union of all or a subset of coordinate points recorded by the positional sensor system 508 during an image capture period that spans multiple shapes, positions, orientations, and/or poses of the elongate device 631 within the anatomic region 750. In these embodiments, the point cloud can include coordinate points captured by the positional sensor system 508 that represent multiple shapes of the elongate device 631 while the elongate device 631 is advanced or moved through patient anatomy during the image capture period. Additionally, or alternatively, because the configuration, including shape and location, of the elongate device 631 within the patient 503 may change during the image capture period due to anatomical motion, the point cloud in some embodiments can comprise a plurality of coordinate points 862 captured by the positional sensor system 508 that represent the shapes of the elongate device 631 as the elongate device 631 passively moves within the patient 503. As described in greater detail below, a point cloud of coordinate points captured by the positional sensor system 508 can be registered to different models or datasets of patient anatomy.

Referring again to FIG. 6, the endoscopic imaging system 509 of the medical instrument system 504 includes one or more image capture devices 647 configured to capture one or more real navigational images of real patient anatomy (e.g., the anatomic passageways 752 of FIG. 7) while the elongate device 631 and/or the medical instrument 632 is within an anatomic region (e.g., the anatomic region 750 of FIG. 7) of the patient 503. For example, the endoscopic imaging system 509 can include an image capture device 647 positioned at the distal portion 637 of the medical instrument 632. In these and other embodiments, the endoscopic imaging system 509 can include one or more image capture devices (not shown) positioned at other locations along the medical instrument 632 and/or along the elongate device 631 (e.g., at the distal portion 638 of the elongate device 631).

In the embodiment illustrated in FIG. 7, the image capture device 647 of the medical instrument 632 (FIG. 6) is advanced to and positioned at the distal portion 638 of the elongate device 631. In this embodiment, the image capture device 647 can survey the anatomic passageways 752 by capturing real navigational images of the anatomic passageways 752 while the elongate device 631 is navigated through the trachea 754 and the bronchial tubes 756 of the anatomic region 750.

FIG. 9 is an example of a real navigational image 970 (e.g., a still image, an image frame of a video, etc.) of patient anatomy of the anatomic region 750 of FIG. 7 (such as one of the anatomic passageways 752) captured via the image capture device 647 (FIG. 7). As shown, the real navigational image 970 shows a branching point or carina 971 of two anatomic passageways 752 within the anatomic region 750 from a viewpoint of the medical instrument 632 (FIG. 6). In this example, because the image capture device 647 is positioned at the distal portions 637 and 638 of the medical instrument 632 and the elongate device 631 (FIG. 7), respectively, the viewpoint of the real navigational image 970 is from the distal portion 637 of the medical instrument 632 such that the medical instrument 632 and the elongate device 631 are not visible within the real navigational image 970. In other embodiments, the image capture device 647 can be positioned at another location along the medical instrument 632 and/or along the elongate device 631 (FIGS. 6 and 7). In these embodiments, the endoscopic imaging system 99 (FIG. 6) can capture real navigational images from a corresponding viewpoint of the medical instrument 632 and/or of the elongate device 631. A portion of the medical instrument 632 and/or of the elongate device 631 may be visible within these real navigational images depending on the positions of the medical instrument 632 and the elongate device 631 relative to one another.

Referring again to FIG. 6, the real navigational images captured by the endoscopic imaging system 509 can facilitate navigation of the distal portion 638 of the elongate device 631 through patient anatomy (e.g., through the anatomic passageways 752 of FIG. 7) and/or delivery of the distal portion 638 of the elongate device 631 to a target location within the patient 503. In these and other embodiments, the real navigational images captured by the endoscopic imaging system 509 can facilitate (i) navigation of the distal portion 637 of the medical instrument 632 beyond the distal portion 638 of the elongate device 631, (ii) delivery of the distal portion 637 of the medical instrument 632 to a target location within the patient 503, and/or (iii) visualization of patient anatomy during a medical procedure. In some embodiments, each real navigational image captured by the endoscopic imaging system 509 can be associated with a time stamp and/or a position recorded in the medical instrument frame of reference ($X_M$, $Y_M$, $Z_M$). The real navigational images captured by the endoscopic imaging system 509 can optionally be used to improve a registration between a point cloud of coordinate points (e.g., the point cloud 860 of FIG. 8) generated by the positional sensor system 508 and image data captured by the imaging system 518.

As shown in FIG. 6, the imaging system 518 is arranged near the patient 503 to obtain three-dimensional images of the patient 503 (e.g., of the anatomic region 750 of FIG. 7). In some embodiments, the imaging system 518 includes one or more imaging technologies, including CT, MRI, fluoroscopy, thermography, ultrasound, OCT, thermal imaging, impedance imaging, laser imaging, nanotube X-ray imaging, and/or the like. The imaging system 518 is configured to generate image data of patient anatomy before, during, and/or after the elongate device 631 is extended within the patient 503. Thus, the imaging system 518 can be configured to capture preoperative, intraoperative, and/or postoperative three-dimensional images of patient anatomy. In these and other embodiments, the imaging system 518 may provide real-time or near real-time images of patient anatomy.

FIG. 10 illustrates an example of intraoperative image data 1080 of a portion 1055 of the anatomic region 750 of FIG. 7 captured during an image capture period by the imaging system 518 (FIG. 6) while the elongate device 631 of the medical instrument system 504 is extended within the anatomic region 750. As shown, the image data 1080 includes graphical elements 1081 representing the elongate device 631 and graphical elements 1082 representing the anatomic passageways 752 of the anatomic region 750.

All or a portion of the graphical elements 1081 and 1082 of the image data 1080 can be segmented and/or filtered to generate a virtual, three-dimensional model of the anatomic passageways 752 within the portion 1055 of the anatomic region 750 (with or without the medical instrument system 504). In some embodiments, the graphical elements 1081 and 1082 can additionally or alternatively be segmented and/or filtered to generate an image point cloud (not shown) of the medical instrument system 504 based, at least in part, on images captured by the imaging system 108 (FIG. 6) while the medical instrument system 504 is within the anatomic region 750. During the segmentation process, pixels or voxels generated from the image data 1080 may be partitioned into segments or elements or be tagged to indicate that they share certain characteristics or computed properties such as color, density, intensity, and texture. The segments or elements may then be converted to an anatomic model and/or to an image point cloud of the medical instrument system 504. Additionally, or alternatively, the segments or elements can be used to locate (e.g., calculate) and/or define a center line or other points running along the anatomic passageways 752. The generated anatomic model and/or the image point cloud may be two or three-dimensional and may be generated in an image reference frame ($X_I$, $Y_I$, $Z_I$).

As discussed above with respect to FIG. 5, the display system 510 (FIG. 5) of the medical system 500 (FIG. 5) can display various images or representations of patient anatomy and/or of the medical instrument system 504 based, at least in part, on data captured and/or generated by the positional sensor system 508, by the endoscopic imaging system 509, by the imaging system 518, and/or by the virtual visualization system 515. In various implementations, the images and/or representations can be utilized by the system to aid the operator 505 (FIG. 5) in conducting an image-guided medical procedure.

Figure 11:
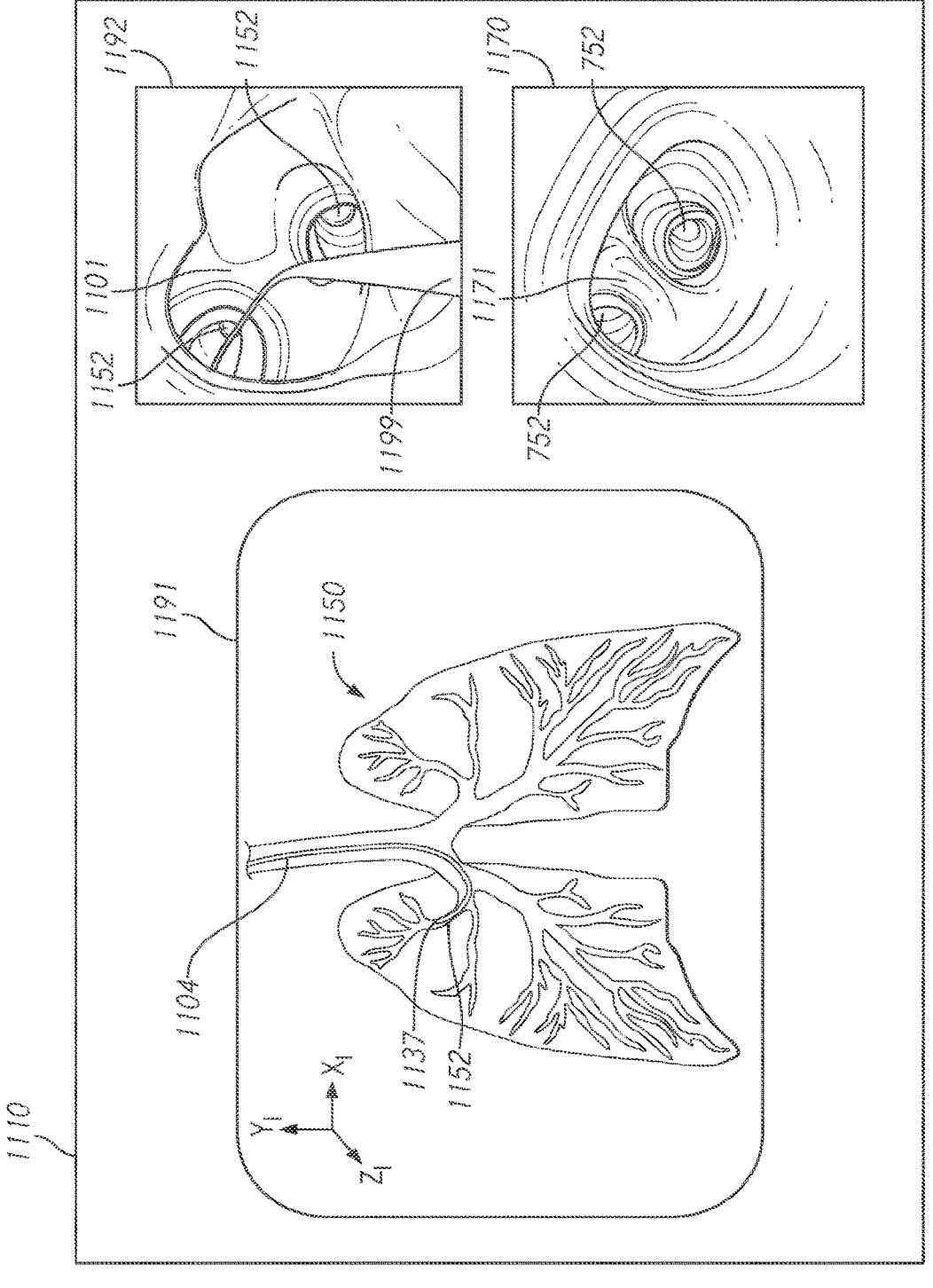
FIG. 11 is a schematic representation of a display of a display system displaying a composite virtual navigational image in which the medical instrument system of FIGS. 6 and 7 is registered to an anatomic model of the anatomic region of FIG. 7, a virtual navigational image of virtual patient anatomy, and a real navigational image of real patient anatomy within the anatomic region in accordance with various embodiments of the present technology.

FIG. 11, for example, is a schematic representation of an example display 1110 produced by the display system 510 (FIG. 5) in accordance with various embodiments of the present technology. As shown, the display 1110 includes a real navigational image 1170, a composite virtual naviga-tional image 1191 (also referred to as a "composite virtual image 1191"), and a virtual navigational image 1192. The real navigational image 1170 can be substantially the same as the real navigational image 970 of FIG. 9. Thus, for example, the real navigational image 1170 can be captured by the endoscopic imaging system 509 (FIG. 6) and pro-vided to the display system 510 (FIG. 5) to be presented on the display 1110 in real-time or near real-time. In the illustrated embodiment, the real navigational image 1170 illustrates real patient anatomy (e.g., a carina 1171 marking a branching point of two anatomic passageways 752) from a viewpoint oriented distally away from the distal portion 637 of the medical instrument 632 (FIG. 6).

The composite virtual image 1191 of FIG. 11 is displayed in the image reference frame ($X_I$, $Y_I$, $Z_I$) and includes an anatomic model 1150 generated from image data of the anatomic region 750 of FIG. 7 captured by the imaging system 518 (FIG. 6). The anatomic model 1150 is registered (i.e., dynamically referenced) with a point cloud of coordi-nate points (e.g., the point cloud 860 of FIG. 8) generated by the positional sensor system 508 (FIG. 6) to display a representation 1104 within the anatomic model 1150 of the tracked position, shape, pose, orientation, and/or movement of the medical instrument system 504 (e.g., of the elongate device 631 of FIG. 6) within the patient 503 (FIG. 6). In some embodiments, the composite virtual image 1191 is generated by the virtual visualization system 515 (FIG. 5) of the control system 512 (FIG. 5). Generating the composite virtual image 1191 involves registering the image reference frame ($X_I$, $Y_I$, $Z_I$) with the surgical reference frame ($X_S$, $Y_S$, $Z_S$) and/or to the medical instrument reference frame ($X_M$, $Y_M$, $Z_M$). This registration may rotate, translate, or otherwise manipulate by rigid and/or non-rigid transforms coordinate points of the point cloud (e.g., the coordinate points 862 of the point cloud 860 of FIG. 8) captured by the positional sensor system 508 to align the coordinate points with the anatomic model 1150. The registration between the image and surgical/instrument frames of reference may be achieved, for example, by using a point-based ICP tech-nique, as described in U.S. Provisional Pat. App. Nos. 62/205,440 and No. 62/205,433, which are both incorpo-rated by reference herein in their entireties. In other embodi-ments, the registration can be achieved using another point cloud registration technique.

Based, at least in part, on the registration, the virtual visualization system 515 can additionally or alternatively generate virtual navigational images (e.g., the virtual navi-gational image 1192 of FIG. 11) that include a virtual depiction of patient anatomy from a viewpoint of a virtual camera on the representation 1104 of the medical instrument system 504 (FIG. 7) within the anatomic model 1150. In the embodiment illustrated in FIG. 11, the virtual camera of the virtual navigational image 1192 is positioned at a distal portion 1137 of the representation 1104 such that (i) the virtual viewpoint of the virtual navigational image 1192 is directed distally away from the distal portion 1137 of the representation 1104 and (ii) the representation 1104 is not visible within the virtual navigational image 1192. In other embodiments, the virtual visualization system 515 can posi-tion the virtual camera (a) at another location along the representation 1104 and/or (b) in a different orientation such that the virtual navigational image 1192 has a corresponding virtual viewpoint. In some embodiments, depending on the position and orientation of the virtual camera and on the positions of the elongate device 631 and the medical instru-ment 632 relative to one another within the patient 503, the virtual visualization system 515 can render a virtual repre-sentation (not shown) of at least a portion of the elongate device 631 and/or of the medical instrument 632 into the virtual navigational image 1192.

In some embodiments, the virtual visualization system 515 can place the virtual camera within the anatomic model 1150 at a position and orientation corresponding to the position and orientation of the image capture device 647 within the patient 503 (FIG. 6). As further shown in FIG. 11, the virtual navigational image 1192 illustrates virtual patient anatomy, such as a carina 1101 marking a branching point of two anatomic passageways 1152 of the anatomic model 1150, from substantially the same location at which the real navigational image 1170 is captured by the image capture device 647 (FIG. 6). Thus, the virtual navigational image 1192 provides a rendered estimation of patient anatomy visible to the image capture device 647 at a given location within the anatomic region 750 of FIG. 7. Because the virtual navigational image 1192 is based, at least in part, on the registration of a point cloud generated by the positional sensor system 508 and image data captured by the imaging system 518, the correspondence between the virtual navi-gational image 1192 and the real navigational image 1170 provides insight regarding the accuracy of the registration and can be used to improve the registration. Furthermore, the real navigational images (e.g., the real navigational image 1170) captured by the endoscopic imaging system 509 (FIG. 6) can (a) provide information regarding the position and orientation of the medical instrument system 504 (FIG. 5) within the patient 503, (b) provide information regarding portions of an anatomic region actually visited by the medical instrument system, and/or (c) help identify patient anatomy (e.g., branching points of anatomic pas-sageways) proximate the medical instrument system 504, any one or more of which can be used to improve the accuracy of the registration.

As further shown in FIG. 11, the virtual navigational image 1192 can optionally include a navigation path overlay 1199. In some embodiments, the navigation path overlay 1199 is used to aid an operator 505 (FIG. 5) to navigate the medical instrument system 504 (FIG. 5) through anatomic passageways of an anatomic region to a target location within a patient 503. For example, the navigation path overlay 1199 can illustrate a "best" path through an ana-tomic region for an operator 505 to follow to deliver the distal portions 637 and/or 638 of the medical instrument 632 and/or of the elongate device 631, respectively, to a target location within the patient 503. In some embodiments, the navigation path overlay 1199 can be aligned with a center-line of or another line along (e.g., the floor of) a correspond-ing anatomic passageway.

C. CONCLUSION

The systems and methods described herein can be pro-vided in the form of tangible and non-transitory machine-readable medium or media (such as a hard disk drive, hardware memory, etc.) having instructions recorded thereon for execution by a processor or computer. The set of instructions can include various commands that instruct the computer or processor to perform specific operations such as the methods and processes of the various embodiments described here. The set of instructions can be in the form of a software program or application. The computer storage media can include volatile and non-volatile media, and removable and non-removable media, for storage of infor-mation such as computer-readable instructions, data structures, program modules or other data. The computer storage media can include, but are not limited to, RAM, ROM, EPROM, EEPROM, flash memory or other solid-state memory technology, CD-ROM, DVD, or other optical storage, magnetic disk storage, or any other hardware medium which can be used to store desired information and that can be accessed by components of the system. Components of the system can communicate with each other via wired or wireless communication. The components can be separate from each other, or various combinations of components can be integrated together into a monitor or processor or contained within a workstation with standard computer hardware (for example, processors, circuitry, logic circuits, memory, and the like). The system can include processing devices such as microprocessors, microcontrollers, integrated circuits, control units, storage media, and other hardware.

Although many of the embodiments are described above in the context of navigating and performing medical procedures within lungs of a patient, other applications and other embodiments in addition to those described herein are within the scope of the present technology. For example, unless otherwise specified or made clear from context, the devices, systems, methods, and computer program products of the present technology can be used for various image-guided medical procedures, such as medical procedures performed on, in, or adjacent hollow patient anatomy, and, more specifically, in procedures for surveying, biopsying, ablating, or otherwise treating tissue within and/or proximal the hollow patient anatomy. Thus, for example, the systems, devices, methods, and computer program products of the present disclosure can be used in one or more medical procedures associated with other patient anatomy, such as the bladder, urinary tract, GI system, and/or heart of a patient.

This disclosure describes various instruments and portions of instruments in terms of their state in three-dimensional space. As used herein, the term "position" refers to the location of an object or a portion of an object in a three-dimensional space (e.g., three degrees of translational freedom along Cartesian x-, y-, and z-coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an object.

As used herein, the term "operator" shall be understood to include any type of personnel who may be performing or assisting a medical procedure and, thus, is inclusive of a physician, a surgeon, a doctor, a nurse, a medical technician, other personnel or user of the technology disclosed herein, and any combination thereof. Additionally, or alternatively, the term "patient" should be considered to include human and/or non-human (e.g., animal) patients upon which a medical procedure is being performed.

From the foregoing, it will be appreciated that specific embodiments of the technology have been described herein for purposes of illustration, but well-known structures and functions have not been shown or described in detail to avoid unnecessarily obscuring the description of the embodiments of the technology. To the extent any materials incorporated herein by reference conflict with the present disclosure, the present disclosure controls. Where the context permits, singular or plural terms can also include the plural or singular term, respectively. Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. As used herein, the phrase "and/or" as in "A and/or B" refers to A alone, B alone, and both A and B. Where the context permits, singular or plural terms can also include the plural or singular term, respectively. Additionally, the terms "comprising," "including," "having" and "with" are used throughout to mean including at least the recited feature(s) such that any greater number of the same feature and/or additional types of other features are not precluded.

Furthermore, as used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result.

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology, as those skilled in the relevant art will recognize. For example, while steps are presented in a given order, alternative embodiments can perform steps in a different order. As another example, various components of the technology can be further divided into subcomponents, and/or various components and/or functions of the technology can be combined and/or integrated. Furthermore, although advantages associated with certain embodiments of the technology have been described in the context of those embodiments, other embodiments can also exhibit such advantages, and not all embodiments need necessarily exhibit such advantages to fall within the scope of the technology.

It should also be noted that other embodiments in addition to those disclosed herein are within the scope of the present technology. For example, embodiments of the present technology can have different configurations, components, and/or procedures in addition to those shown or described herein. Moreover, a person of ordinary skill in the art will understand that these and other embodiments can be without several of the configurations, components, and/or procedures shown or described herein without deviating from the present technology. Accordingly, the disclosure and associated technology can encompass other embodiments not expressly shown or described herein.

What is claimed is:
1. A system for performing a medical procedure within an anatomic region of a patient, the system comprising:

a medical instrument configured to be inserted within the anatomic region, the medical instrument including an image capture device;

a processor operably coupled to the image capture device; and a memory operably coupled to the processor and storing instructions that, when executed by the processor, cause the system to perform operations comprising:

receiving a three-dimensional (3D) model of the anatomic region, the 3D model including a model landmark corresponding to an anatomic landmark in the anatomic region;

obtaining, via the image capture device, pose information for the image capture device and a plurality of images of the anatomic landmark, wherein at least some of the images represent different views of the anatomic landmark;

determining, based on the pose information and the plurality of images, a set of transformation parameters for aligning a frame of reference for the image capture device with a frame of reference for the 3D model; and registering the frame of reference for the 3D model to the frame of reference for the image capture device using a registration algorithm, wherein the set of transformation parameters is used as a seed for the registration algorithm.

2. The system of claim 1 wherein the anatomic landmark comprises a main carina of the patient's lungs.

3. The system of claim 1 wherein the anatomic region includes a plurality of branched passageways and the anatomic landmark comprises a branching region of the branched passageways.

4. The system of claim 1 wherein the operations further comprise detecting whether the medical instrument is in proximity to the anatomic landmark.

5. The system of claim 4 wherein detecting whether the medical instrument is in proximity to the anatomic landmark comprises determining whether the anatomic landmark is within a field of view of the image capture device.

6. The system of claim 4 wherein the medical instrument is configured to be inserted within the anatomic region via an elongate tube, and wherein detecting whether the medical instrument is in proximity to the anatomic landmark comprises determining whether a portion of the medical instrument is positioned beyond a distal end of the elongate tube.

7. The system of claim 4 wherein the system is configured to automatically obtain the plurality of images in response to detecting that the medical instrument is in proximity to the anatomic landmark.

8. The system of claim 1 wherein obtaining the plurality of images comprises moving the image capture device to a plurality of different locations relative to the anatomic landmark.

9. The system of claim 8 wherein the system is configured to automatically move the image capture device to the plurality of different locations.

10. The system of claim 8 wherein the operations further comprise outputting instructions configured to guide an operator in moving the image capture device to the plurality of different locations.

11. The system of claim 1 wherein determining the set of transformation parameters includes:

generating, based on the images, a three-dimensional (3D) representation of the anatomic landmark; and aligning the 3D representation of the anatomic landmark with the 3D model.

12. The system of claim 11 wherein the 3D representation is generated using one or more of the following: a shape from shading algorithm, a structure from motion algorithm, a single-shot depth estimation algorithm, or an end-to-end depth reconstruction algorithm.

13. The system of claim 11 wherein the medical instrument includes a positional sensor and the 3D representation is generated based, at least partly, on position data received from the positional sensor.

14. The system of claim 13 wherein the positional data represents one or more locations of the image capture device when the images of the anatomic landmark were obtained.

15. The system of claim 11 wherein aligning the 3D representation of the anatomic landmark with the 3D model comprises determining a correspondence between at least one surface feature of the 3D representation and at least one corresponding surface feature of the 3D model.

16. The system of claim 11 wherein aligning the 3D representation of the anatomic landmark with the 3D model comprises performing an initial registration between the 3D representation and the 3D model.

17. The system of claim 1 wherein determining the set of transformation parameters includes:

generating, using the 3D model, at least one two-dimensional (2D) virtual view of the model landmark; and determining a correspondence between at least one of the images and the at least one 2D virtual view.

18. A non-transitory, computer-readable medium storing instructions thereon that, when executed by one or more processors of a computing system, cause the computing system to perform operations comprising:

receiving a three-dimensional (3D) model of an anatomic region, the 3D model including a model landmark corresponding to an anatomic landmark in the anatomic region;

obtaining, via an image capture device within the anatomic region, pose information for the image capture device and a plurality of images of the anatomic landmark, wherein at least some of the images represent different views of the anatomic landmark;

determining, based on the pose information and the plurality of images, a set of transformation parameters for aligning a frame of reference for the image capture device with a frame of reference for the 3D model; and registering the frame of reference for the 3D model to the frame of reference for the image capture device using a registration algorithm, wherein the set of transformation parameters is used as a seed for the registration algorithm.

19. The non-transitory, computer-readable medium of claim 18 wherein the operations further comprise outputting feedback configured to guide an operator in improving image quality.

20. The non-transitory, computer-readable medium of claim 19 wherein the feedback includes a recommended action including one or more of the following: defogging the image capture device, clearing body fluid from the image capture device, or moving the image capture device away from airway walls within the anatomic region.

* * * * *